(12) United States Patent
Bauer

(10) Patent No.: US 12,150,475 B2
(45) Date of Patent: Nov. 26, 2024

(54) SMOKING APPARATUS AND METHOD

(71) Applicant: David Carl Bauer, Kirdwood, MO (US)

(72) Inventor: David Carl Bauer, Kirdwood, MO (US)

( * ) Notice: Subject to any disclaimer, the term of this patent is extended or adjusted under 35 U.S.C. 154(b) by 760 days.

(21) Appl. No.: 17/258,756

(22) PCT Filed: Sep. 24, 2019

(86) PCT No.: PCT/US2019/052590
§ 371 (c)(1),
(2) Date: Jan. 8, 2021

(87) PCT Pub. No.: WO2020/068743
PCT Pub. Date: Apr. 2, 2020

(65) Prior Publication Data
US 2022/0346439 A1   Nov. 3, 2022

Related U.S. Application Data

(60) Provisional application No. 62/735,741, filed on Sep. 24, 2018.

(51) Int. Cl.
*A24F 1/02* (2006.01)
*A24D 3/16* (2006.01)
(Continued)

(52) U.S. Cl.
CPC .................. *A24F 1/02* (2013.01); *A24D 3/16* (2013.01); *A24D 3/163* (2013.01); *A24F 1/32* (2013.01); *A24F 40/53* (2020.01); *A61M 15/06* (2013.01)

(58) Field of Classification Search
CPC .... A24F 1/02; A24F 1/32; A24F 40/53; A24F 1/30; A24D 3/16; A24D 3/163;
(Continued)

(56) References Cited

U.S. PATENT DOCUMENTS 10,973,258 B2 * 4/2021 Alarcon ............ A61M 15/0083
2009/0260645 A1   10/2009 Brotton et al.
(Continued)

FOREIGN PATENT DOCUMENTS

CN            207767550 U  *  8/2018  ........... A24F 40/485

OTHER PUBLICATIONS

International Search Report and Written Opinion issued in PCT/US2019/052590, dated Dec. 10, 2019, 16 pages.

*Primary Examiner* — Truc T Nguyen
(74) *Attorney, Agent, or Firm* — Stinson LLP

(57) ABSTRACT

Apparatus consistent with the present disclosure may be a pipe that includes heat transfer materials that have a thermal conductivity of greater than 50 Watts per meter Kelvin. Heat transfer materials may include one or more solid heat sinks (that are rigidly connected to each other or to a portion of the pipe), Peltier devices, or loose fill of a desired size or shape. Fill included in the pipe may also absorb particulate matter or volatile organic compounds. As a user burns or vaporizes materials at one end of the pipe and sucks heated smoke or vapor into the pipe, that user may inhale cool and clean smoke or vapor. Methods and apparatus consistent with the present disclosure may allow a controller at the pipe to send sensor or consumption data to other electronic devices when a number of milligrams of a substance inhaled by a patient are monitored.

23 Claims, 14 Drawing Sheets

(51) Int. Cl.
*A24F 1/32* (2006.01)
*A24F 40/53* (2020.01)
*A61M 15/06* (2006.01)

(58) Field of Classification Search
CPC .. A61M 15/06; A61M 11/003; A61M 11/041; A61M 15/008; A61M 2016/0021; A61M 2202/0225; A61M 2202/0233; A61M 2205/0205; A61M 2205/3368; A61M 2205/3553; A61M 2205/3569; A61M 2205/3592; A61M 2205/3606; A61M 2205/3673; A61M 2205/505; A61M 2205/52; A61M 2205/584; A61M 2205/75; A61M 2205/8206; A61M 2206/14

See application file for complete search history.

(56) References Cited

U.S. PATENT DOCUMENTS

| | | |
|---|---|---|
| 2012/0266900 A1 | 10/2012 | El-Deiry |
| 2015/0142387 A1* | 5/2015 | Alarcon ............ A61M 15/0083 702/187 |
| 2015/0209530 A1* | 7/2015 | White .................. A24D 1/20 128/200.23 |
| 2017/0238610 A1* | 8/2017 | Reevell .................. G06F 1/04 |
| 2018/0043114 A1 | 2/2018 | Bowen et al. |
| 2019/0174833 A1 | 6/2019 | Shuster et al. |
| 2022/0183389 A1* | 6/2022 | Carmichael ............ A24F 40/60 |

* cited by examiner

Screen Perspective View

Screen Top View

Screen Side View

SMOKING APPARATUS AND METHOD

CROSS REFERENCE TO RELATED APPLICATIONS

This application is the U.S. national stage application of International Patent Application No. PCT/US2019/052590, filed Sep. 24, 2019, and which claims the benefit of U.S. provisional patent application No. 62/735,741, filed Sep. 24, 2018, the entire disclosures of which are incorporated herein by reference.

BACKGROUND OF THE INVENTION

Field of Invention

The present disclosure is generally directed to cooling heated materials. More specifically, the present disclosure relates to methods and apparatus that reduces the temperature of combusted or vaporized materials as smoke or vapors move from a source to an output. Methods and apparatus consistent with the present disclosure may also remove volatile organic compounds (VOCs) and particles from the smoke or vapors.

Description of the Related Art

For hundreds to thousands of years peoples of the world have smoked or consumed plant based or plant derived materials using various different types of apparatus and methods. Tobacco, *cannabis*, hashish, peyote, nicotine concentrates, *cannabis* extracts, and other plant based substances have been smoked after plant material has been placed in a pipe or encased in paper (e.g. rolled in a cigarette, joint, or blunt). Recently vaporizers have been developed that vaporize nicotine and *cannabis* concentrates and extracts. Each of these different smoking apparatus heat plant materials or plant derived materials to temperatures that exceed several hundred degrees Fahrenheit (e.g. 400° F.). These conventional methods and apparatus provide smoke or vapor to the lungs of a person at temperatures that also approach or exceed 400° F.

Pipes come in two basic forms, one in which a substance is burned/combusted after which heated smoke passed through a tube into the mouth and lungs of a person as that person inhales. A second form of pipe commonly referred to as a water pipe, a bong, or a hookah may hold water through which heated smoke is passed when a person burns plant matter contained in a bowl as that person inhales the smoke. The first form of pipe causes one to inhale unfiltered heated smoke. While many believe that water included in a water pipe, bong, or hookah filters and cools heated smoke, in reality water in these pipes provide little or no actual cooling or filtering of the heated smoke. First of all water has a very low heat transfer capabilities of about 0.8 Watts per meter Kelvin (W/m K) at room temperature (e.g. 70° F.) and about 1.8 W/m K at the temperature of ice water (e.g. 32° F.). While the water in a water pipe does become dirty after smoking, much of the dirt that comes from ash that has fallen into the water from a bowl and not from VOCs and small particles (e.g. micro-partides or nanopartides) in the heated smoke. In instances when water pipes are made of glass, the glass thermally insulates the inside of the water pipe from outside of the water pipe, so what little heat transferred to the water would be trapped there in a glass water pipe. As such, water pipes are incapable effectively cooling heated smoke or vapor.

Some other forms of pipes vaporize cannabinoids from concentrates (e.g. distillates or isolates), such pipes may include a metal piece that is heated with a flame and a small portion of a concentrate is placed on the heated metal piece. Distillates are extracts that contain other elements besides a desired compound or a specific set of one or more cannabinoids, distillates often contain somewhere between 50 and 80% of at least one desired compound and they contain other materials extracted from the plant matter (e.g. waxes or terpenes). Isolates are extracts that are substantially pure and may contain in excess of 90% of a single desired compound (e.g. a single set of one or more cannabinoids). The rapid heating of the concentrate causes elements included in the concentrate to vaporize and a person inhales the heated vapors through a tube of the pipe. Here again, temperatures of the inhaled vapors may approach or exceed 400° F. The same is true in instances when plant materials are encased in paper and then smoked. Recent news reports indicate that young individuals inhaling nicotine, cannabinoids, flavorings, or vitamin E acetate using a vaporizer have suffered lung damage. Even though no one yet knows what factors have caused this reported lung damage, temperature is a factor that likely contributes to lung or blood vessel damage in the lungs of smokers. Even when a filter or a when a cigarette holder is used, temperatures of heated smoke may approach or exceed 400° F.

While *cannabis* may be consumed by persons, eating prepared cannabinoid containing materials in capsules or in edible preparations (e.g. chocolates, gummies, brownies, or other), some who wish to consume *cannabis* or that are compelled to consume *cannabis* because of health needs, do not tolerate or may not like consuming cannabinoid preparations by mouth. Edibles also can be easily mistaken as being a food or candy by children or others and this may cause those children or others to consume cannabinoids by mistake. Such mistakes may not be immediately identified because when cannabinoids are eaten, it takes time for them to be digested and the onset of effects may initially be gradual.

Another problem associated with the smoking or vaping of *cannabis* plant matter or concentrates is that a patient and their doctor have no idea of how many milligrams of specific cannabinoids were consumed by the patient over time. This is because current smoking apparatus have no capability of measuring or estimating how many milligrams of specific cannabinoids were inhaled by a person when they smoke or vape.

What are needed are new apparatus and methods that cool smoke or vapor so that people can inhale desired compounds at lower temperatures. What are needed are new apparatus and methods that remove volatile organic compounds from burnt or vaporized materials before they are inhaled by a person. Furthermore, what are needed are methods and apparatus that identify or estimate cannabinoid dosages that have been inhaled by a patient when they smoke or vape.

SUMMARY OF THE PRESENTLY CLAIMED INVENTION

Figure 1:
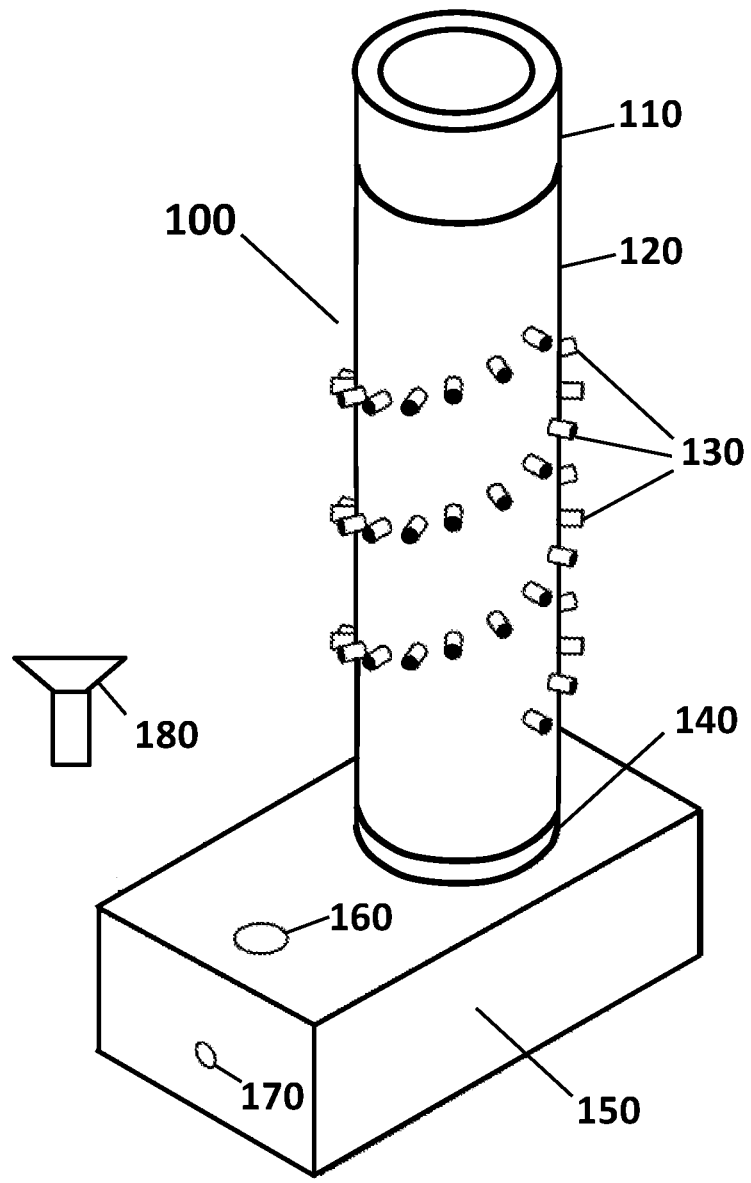
FIG. 1 illustrates a perspective view of a smoking apparatus that passively cools hot smoke or vapor.

Methods and apparatus consistent with the present disclosure relate to cooling heated smoke or vapor and to informing a user of the apparatus when an output temperature is at or above a threshold temperature. An apparatus consistent with the present disclosure may include an input that receives heated smoke or vapor, an output that receives the mouth of a person, one or more chambers that couple the input to the output, and a heat transfer material located in at least one of the chambers. The heat transfer material cooling the smoke or vapor when the person sucks on the output of the apparatus with their mouth.

An apparatus consistent with the present disclosure may receive an indication of a temperature sensed by a temperature sensor located at an output of a smoking apparatus when heated smoke or vapor is sucked through the smoking apparatus. The received indication may be compared with a reference that corresponds to a threshold temperature and the method may also include providing an indication to an output device that identifies that the output temperature at least meets the threshold temperature. The received temperature indication may be a voltage or a current provided by the temperature sensor or may be a digital value representative of the output temperature. The comparison of the temperature indication and the threshold temperature may be performed an electronic circuit or by a processor executing instructions out of a memory.

Another apparatus consistent with the present disclosure may include an input that receives heated smoke or vapor, an output that receives the mouth of a person, one or more chambers that couple the input to the output, and a heat transfer material located in at least one of the chambers. The apparatus may also include a source of electrical energy, a thermoelectric heat transfer device, and a heat transfer material. A cool side of the thermoelectric device and the heat transfer material may cool the smoke or vapor when the person sucks on the output of the apparatus with their mouth.

DETAILED DESCRIPTION

Methods and apparatus consistent with the present disclosure may cool combusted or vaporized materials before they are inhaled by a person. Apparatus consistent with the present disclosure may be a pipe that includes heat transfer materials (heat sinks or other heat absorbing materials) that capture heat. Such heat sinks or heat absorbing materials may transfer heat from an inside portion of the apparatus to an outside portion of the apparatus or may remove particles and volatile organic compounds from heated smoke or vapor as that smoke or vapor is sucked through a chamber. These heat sinks or heat transfer materials may have a thermal conductivity of greater than 50 Watts per meter Kelvin (W/m K). As such, heat transfer materials consistent with the present disclosure include, yet are not limited to aluminum, iron compounds, steel, copper, silver, gold, stainless steel, carbon, graphite, graphene, or graphene foam. Preferred materials may be non-toxic and they may have anti-microbial or anti-bacterial characteristics. Heat sinks include solid manufactured parts such as rods, cylinders, or heat pipes. Such heat sinks may have been manufactured by various means known in the art including, yet not limited to molding, stamping, forming, cutting, or machining. Other heat transfer materials may include a filling material that may be in the form of granules, flakes (flaked materials), powders, foams, or combination thereof. Apparatus consistent with the present disclosure may also filter combusted or vaporized materials when capturing or neutralizing carbon compounds (e.g. carbon dioxide, carbon monoxide, or other carbon compounds) or other materials such as dioxin. This filtering may remove small particles (e.g. micro-particles or nanoparticles) or chemicals (e.g. ammonia) from smoke or vapor.

Apparatus consistent with the present disclosure have been tested by patients who wish to consume cannabinoids by inhalation, yet have not been able to smoke using conventional smoking apparatus without experiencing lung irritation. Patients suffering from asthma and emphysema reported no lung irritation while feeling immediate effects of consuming a cannabinoid when they smoked *cannabis* plant matter using a pipe consistent with the present disclosure. While such results are somewhat anecdotal, they are a call to action to clinically evaluate whether apparatus consistent with the present disclosure can significantly mitigate or eliminate risks associated with conventional smoking. As such a goal is to have apparatus consistent with the present disclosure be tested and approved for use by the Food and Drug Administration (FDA) for applications that include drug delivery to patients. Apparatus consistent with the present disclosure have also have a goal of cooling and cleaning smoke or vapor to significantly mitigate or eliminate risks associated with conventional smoking, such as lung cancer, heart disease, lung irritation, while providing relief to patients with conditions such as asthma, emphysema, or chronic obstructive pulmonary disease (COPD).

FIG. 1 illustrates a perspective view of a smoking apparatus that passively cools hot smoke or vapor. The smoking apparatus or pipe 100 of FIG. 1 includes top portion 110, middle portion 120, base adapter 140, and base portion 150. Base portion 150 includes smoking adapter hole 160 and vent hole 170. In certain instances bowl 180 may be placed into hole 160, plant materials may be placed into bowl 180, and a person may then ignite the plant material with a flame when the plant material is smoked. The user may clear the pipe of smoke or vapor by releasing vent hold 170 while still inhaling. In certain instances pipe 100 of FIG. 1 may be disassembled by unscrewing base adapter 140 from the base portion 150. As such, top portion 110 may be unscrewed from the middle portion 120 of pipe 100. Alternatively, the various portions 110, 120, 140, and 150 may fit together by sliding the portions together. In such instances, the various portions may include tapered edge portions that allow the portions to be fitted together and securely retained. These edges portions may include screens that fit in or over ends of a portion of the pipe and these screens may be used to contain fill materials that may absorb heat and that may filter particles out of smoke or vapor.

The middle portion 120 of pipe 100 includes heat transfer members (e.g. rods or cylinders) 130 that extend from an interior chamber to an outside portion of pipe 100. Heat transfer members 130 (heat sinks) may be metallic rods or cylinders that are designed to transfer heat from smoke or vapor as that smoke or vapor is sucked into the mouth of a person from bowl 180, through hole 160, thorough an base 150, and through portions 140, 120, and 110 of pipe 100. Note that the heat transfer members 130 of FIG. 1 are arranged in a spiral pattern (e.g. in the form of a helix), this spiral pattern may cause smoke or vapor sucked through pipe portion 120 to move in a manner that twists around heat transfer members 130. Heat transfer members 130 may be made of any metallic heat conducting materials that are non-toxic (e.g. aluminum, copper, gold, silver, or stainless steel). Portions 110, 120, or 140 may also be made of materials that transfer heat. In certain instances, members 130 or portions 110, 120, or 140 may be made of non-metallic substances that transfer heat (e.g. materials such as graphite, carbon, or carbon nanotubes).

In certain instances, the middle portion 120 of FIG. 1 may be filled with one or more materials that may include graphite beads, graphite flakes, carbon beads, carbon flakes, charcoal beads, charcoal flakes and/or rocks or minerals with certain properties. Certain of these materials may be used to transfer heat and others may be used to absorb carbon or carbon dioxide or other hazardous materials that may be included in smoke or vapors. In certain instances rocks or minerals that chemically bind carbon dioxide (such as peridotite that transforms CO2 into harmless calcite, lithium hydroxide, or sodium hydroxide) or that absorb heat (such as volcanic rock) may be used. Furthermore, materials such as activate carbon or activated charcoal (e.g. coconut shell charcoal) may be used to absorb adsorb contaminates or heat.

Note that vent (smoke clearing) hole 170 and hole 160 may both be coupled to a same channel internal to base portion 150. This internal channel may connect to inside portions of items 140, 120, and 110 of FIG. 1. When a person smokes plant material placed in bowl 180, they may cover vent hole 170 with their finger, place their mouth over top portion 110, and ignite the plant material with a match or lighter as they suck smoke into and through pipe 100. The person may then remove their finger from vent hole 170 and suck air into pipe 100 when clearing an internal portion of pipe 100 of smoke.

Typically, when combustion is used to ignite plant matter, smoke temperatures may range from 450 degrees Fahrenheit (OF) to nearly 2000° F. When materials such as *cannabis* extracts or nicotine solutions are vaporized and inhaled, substances inhaled using conventional pipes or vaporizers by a person may exceed 400° F. Such high temperatures can scorch human tissue, as such the inhalation of high temperature materials can damage tissue in a person's lungs. Apparatus consistent with the present disclosure are capable of cooling heated smoke or vapor to temperatures below the body temperature of a person while still allowing desired elements to be inhaled into a person's lungs. Temperatures of 90° F. have been observed after *cannabis* materials that include tetrahydrocannabinol (THC) have been combusted or turned into a vapor and passed through an apparatus consistent with the apparatus or pipe 100 of FIG. 1.

Furthermore, patients that are sensitive to inhaling smoke or vapors using conventional pipes or vaporizer pens have reported no adverse side effects when smoking *cannabis* using apparatus consistent with the present disclosure. In such instances, these patients have reported feeling the effects of consuming THC without adverse side effects they feel when they inhale even a small amount of smoke or vapor using conventional pipes. THC is a chemical that is known to begin to vaporize at a temperature of 315 OF at atmospheric pressure. Since distillates (resin) or crystalized (solid) THC are known to begin melting (turning from a plastic like resin or solid) into a liquid form at a temperature of about 90° F. or less, one of ordinary skill in the art at the time of the invention could expect cannabinoids such as THC to condensate into a resin form, a solid form, or a liquid form at temperatures lower than human body temperature. Apparatus consistent with the present disclosure, therefore, provide unexpected results of providing THC to a person through inhalation at temperatures when the THC should be in a liquid or solid form.

While some believe that water included in conventional water pipes cool smoke, in reality water pipes cannot cool smoke much at all. This is because water has poor thermal conductivity (0.8 Watts per meter Kelvin (W/m K) at room temperature and ice water has a thermal conductivity of 1.8 W/m K). At room temperature (24° C./75° F.) water has a thermal conductivity of about 600 milli-Watts per meter Kelvin (mW/m K), where aluminum has a thermal conductivity of about 250 Watts per meter Kelvin (W/m K). As such water has poor heat transfer capabilities as compared to materials used in the presently disclosed apparatus. Another shortcoming of conventional water pipes is that most of them have outer portions that are glass. Since glass is an insulator, any heat transferred to the water cannot escape the glass. Because of this, the repeated smoking of bowl after bowl of plant material in a conventional water pipe will cause the water in the water pipe to heat. Because of the high heat transfer capabilities of the Applicant's heat transfer materials, apparatus consistent with the present disclosure cool smoke or heated vapors much more efficiently than water pipes.

Figure 2:
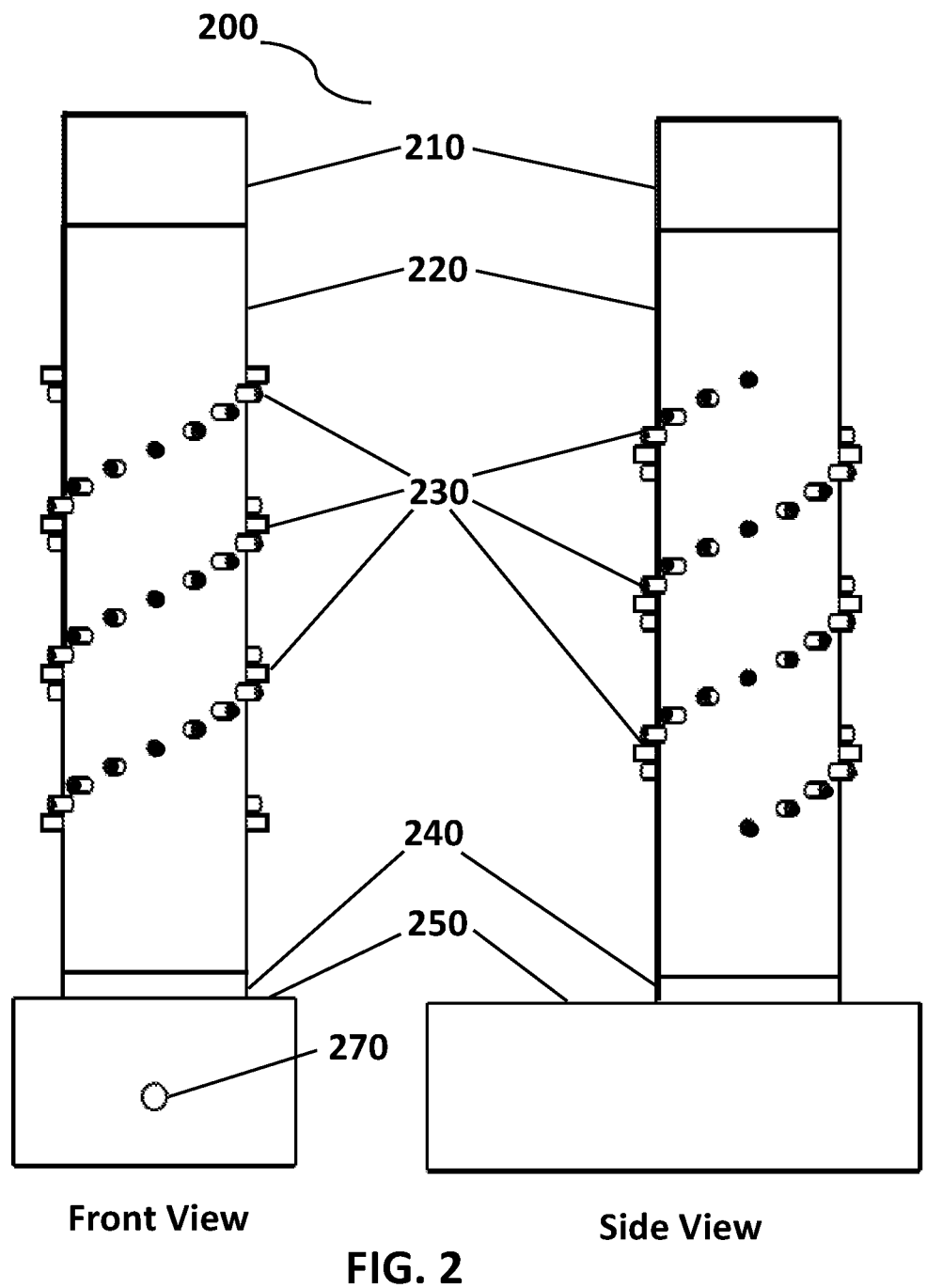
FIG. 2 illustrates a front view and a side view of the apparatus illustrated in FIG. 1.

FIG. 2 illustrates a front view and a side view of the apparatus illustrated in FIG. 1. Note that the front and side views of apparatus 200 of FIG. 2 includes top portion 210, side portion 220, heat transfer mechanisms 230 (heat sinks), bottom adapter portion 240 and base portion 250 that are equivalent to respective portions 110, 120, 130, 140, and 150 of the pipe 100 of FIG. 1. Note also that the font view of apparatus 200 includes vent hole 270. The heat transfer mechanisms 130 of FIG. 1 and 230 of FIG. 2 may allow heat to be transferred from hot smoke or vapor inside of pipe 100 or 200 to outer surfaces pipe 100 or 200. Once this heat has been transferred to these outer surfaces, it may then escape from either pipe 100 or 200 as air that surrounds such pipes is heated. This may be true even when side portion 220 is made from materials that have lower heat transfer coefficients than 50 W/m K as heat transfer mechanisms 130 & 230 includes portions on an outer surface of pipe 100 & 200 respectively.

Figure 3:
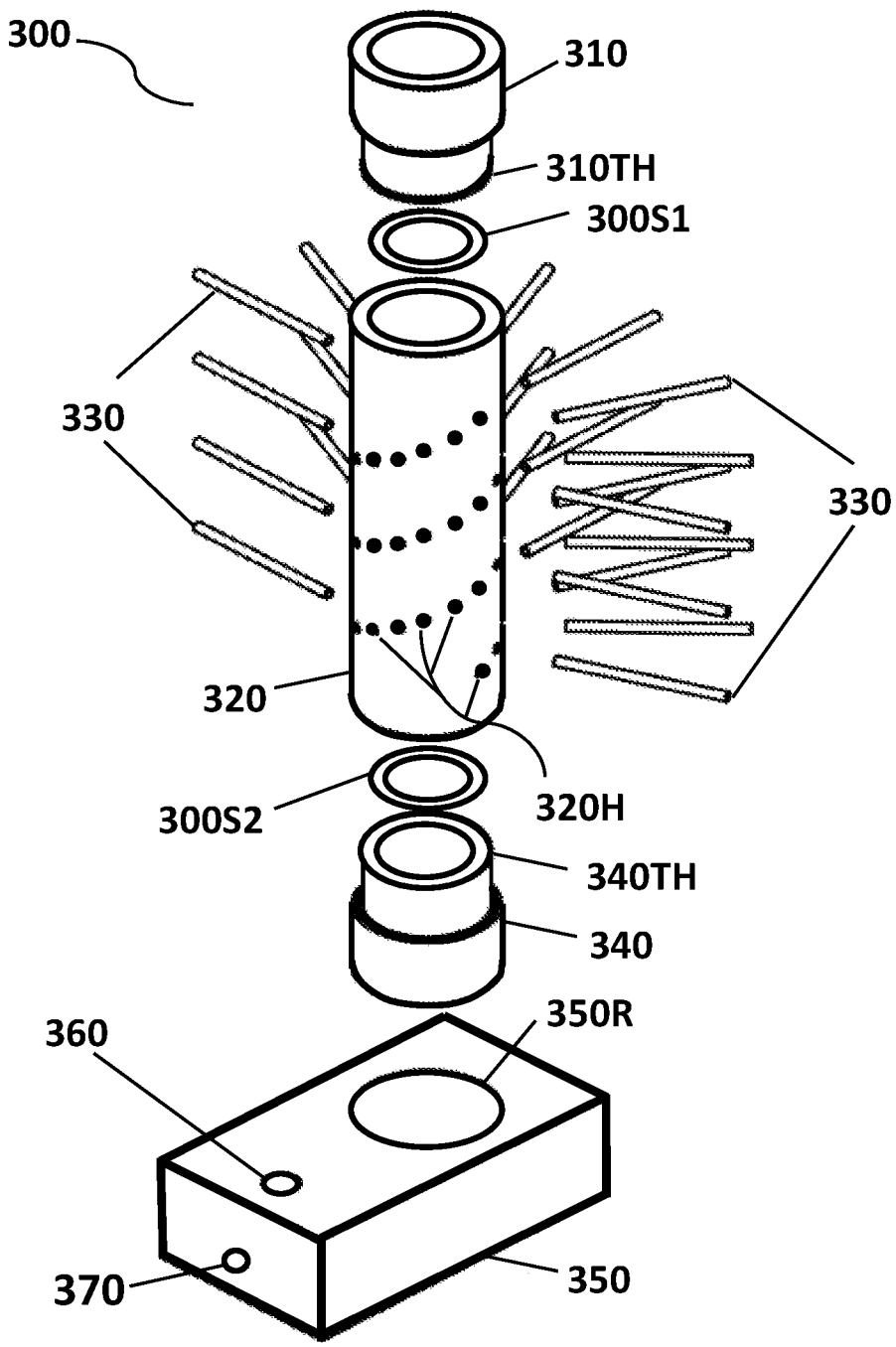
FIG. 3 illustrates a perspective view of an apparatus consistent with the present disclosure before it is assembled.

FIG. 3 illustrates a perspective view of an apparatus consistent with the present disclosure before it is assembled. Apparatus 300 of FIG. 3 includes all of the same parts as apparatus 100 of FIG. 1. Apparatus 300 includes upper portion 310, middle portion 320, adapter portion 340, and base portion 350. Each of these portions 310, 320, 340, and 350 of FIG. 3 may be identical to respective portions of FIG. 1 or FIG. 2 (i.e. respective items 110/210, 120/220, 140/240, and 150/250 of FIGS. 1 and 2). Note that base portion 350 also includes heat transfer mechanisms (heat sinks) 330, hole 360, and vent hole 370.

Apparatus or pipe 300 of FIG. 3 also includes additional parts and features not illustrated in FIG. 1 or in FIG. 2. These parts and features include screen 300S1, screen 300S2, threaded portion 310TH of upper portion 310, threaded portion 340TH of adapter portion 340, and receiver hole 350R of base portion 350. The apparatus 300 of FIG. 3 may be assembled by various methods that include machining, molding, forming, welding, and/or bonding (e.g. press fitting, gluing or ultrasonic bonding). Note that middle portion 320 includes holes 320H through which heat sinks 330 may be passed through when pipe 300 is fabricated. Heat sinks 330 may be permanently attached to portion 320 of FIG. 3. For example, each of these heat sinks may be bonded to portion 320 with a heat conducting glue or epoxy or they may be welded to portion 320 of pipe 300. Adapter portion 340 may be attached to base portion 350 by inserting adapter portion 340 into to receiving hole 350R. Adapter portion 340 may be permanently attached to base portion 350 (e.g. by welding, bonding, or gluing). Alternatively, adapter portion 340 may be remove-ably attached to base portion 350 using any means known in the art (using threads or press fit-fittings).

Screen 300S2 may then be placed on top of adapter 340 and middle portion 320 may be screwed into threads 340H included in adapter 340. In certain instances, materials that absorb heat or that adsorb CO2 (like the aforementioned graphite beads, graphite flakes, carbon beads, carbon flakes, charcoal beads, charcoal flakes and/or rocks or minerals with certain properties) may be a fill that is poured into middle portion 320. Screen 300S2 may keep these particles from falling into base portion 350 through adapter 340. In such instances, holes or openings, in screen 300S2 may be smaller than critical dimensions of pieces of an adsorptive fill. Screens that may be used with apparatus consistent with the present disclosure may have a hole size of about 150 microns). Screen 300S1 may then be placed between upper portion 310 and middle portion 320 when upper portion 310 is screwed into a top part of middle portion 320 using threads 310TH. In instances when middle portion 320 is filled with heat and/or CO2 adsorptive fill, holes or openings in screen 300S1 may also retain the adsorptive fill in middle portion 320 of pipe 300. Screen 300S1 may, thus, hold adsorptive fill within middle portion 320 even when pipe 300 is inverted. In instances when an owner of pipe 300 wishes to replace used adsorptive fill, that owner may unscrew top portion 310 from middle portion 320, then dump the adsorptive fill out, pour new adsorptive fill into middle portion 320, place screen 300S1 between middle portion 320 and top portion 310, and then screw top portion 310 and middle portion 320 back together.

Base portion 350 may also be fabricated by any means known in the art. As such base portion 350 may be made by methods that include one or more of machining, molding, forming, welding, and/or bonding. In certain instances, base portion 350 may be made by drilling hole 350R, by drilling hole 360, and by drilling hole 370 in a solid piece of material. Alternatively, base portion 350 may made from a plurality of different parts that are assembled together by standard means.

Figure 4:
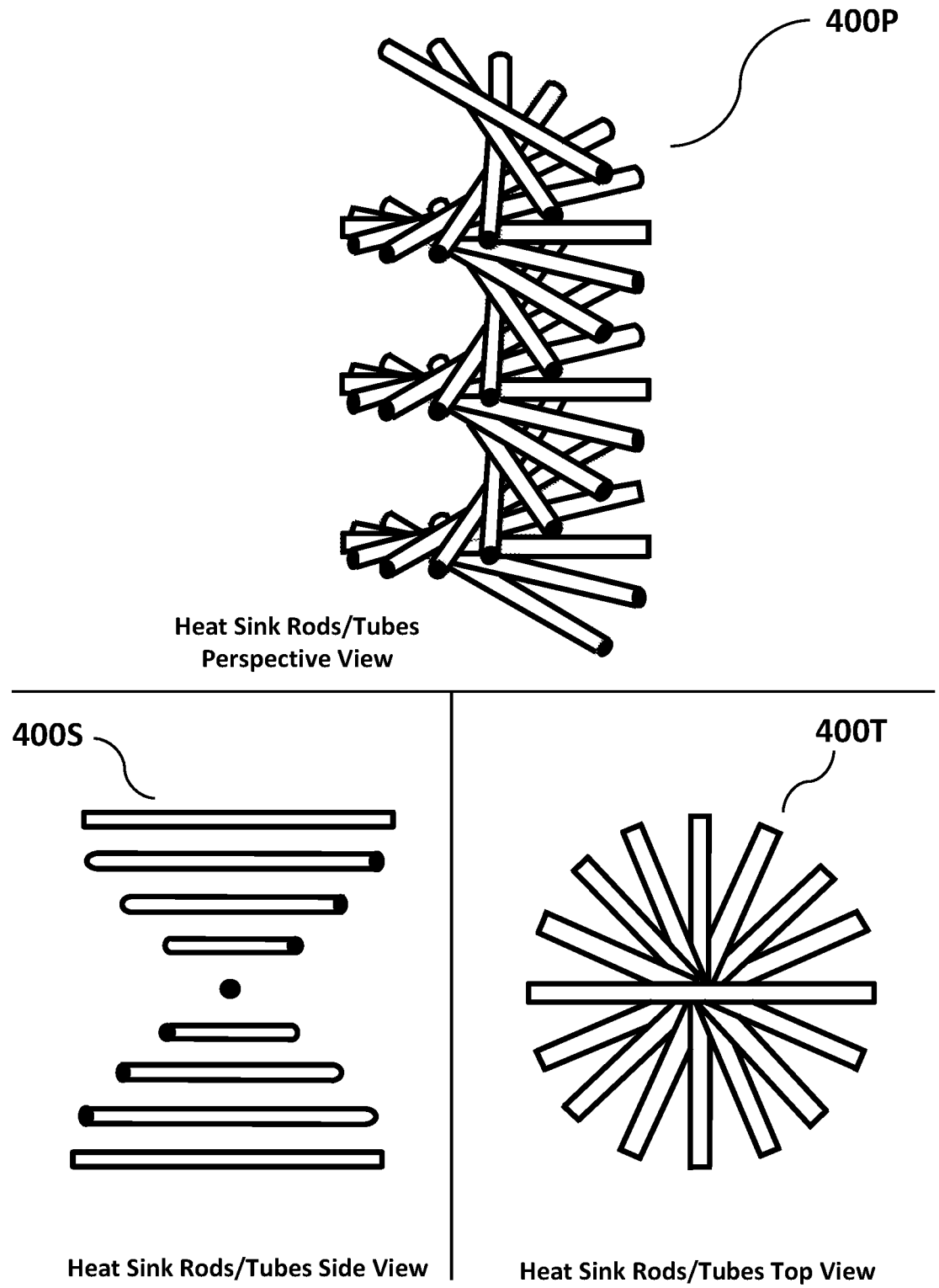
FIG. 4 illustrates three different views of how heat sink rods or tubes may be retained within a middle portion of an apparatus consistent with the present disclosure.

FIG. 4 illustrates three different views of how heat sink rods or tubes may be retained within a middle portion of an apparatus consistent with the present disclosure. FIG. 4 includes perspective view 400P, side view 400S, and top view 400T of the heat transfer mechanisms (sinks) 130, 230, and 300 after they have been assembled into respective pipes 100, 200, and 300 of FIGS. 1-3. For clarity, the walls of a middle portion to which the heat transfer rods/tubes connect are not shown in FIG. 4. Note that the heat sink rods of FIG. 4 form a spiral or twisting/helical pattern that would force smoke or vapor to curl around to dramatically increases effective surface area to remove heat from the smoke or vapor when a person sucks that smoke or vapor through a pipe, such as pipes 100, 200, or 300 of FIGS. 1-3.

Figure 5:
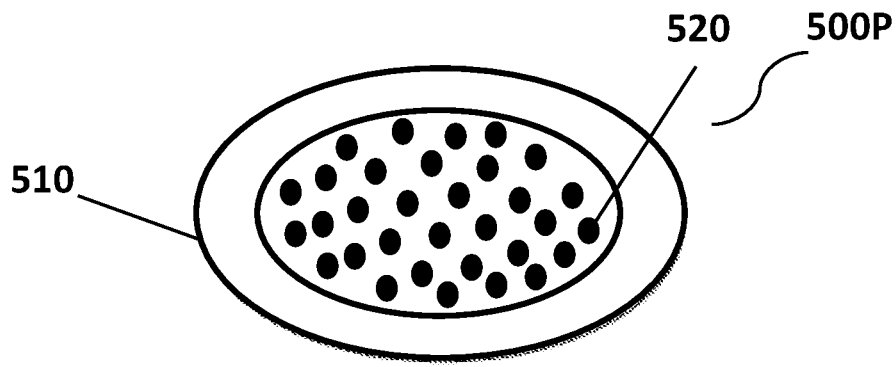
FIG. 5 illustrates 3 different views of screens that may be used with apparatus consistent with the present disclosure.
Figure 5:
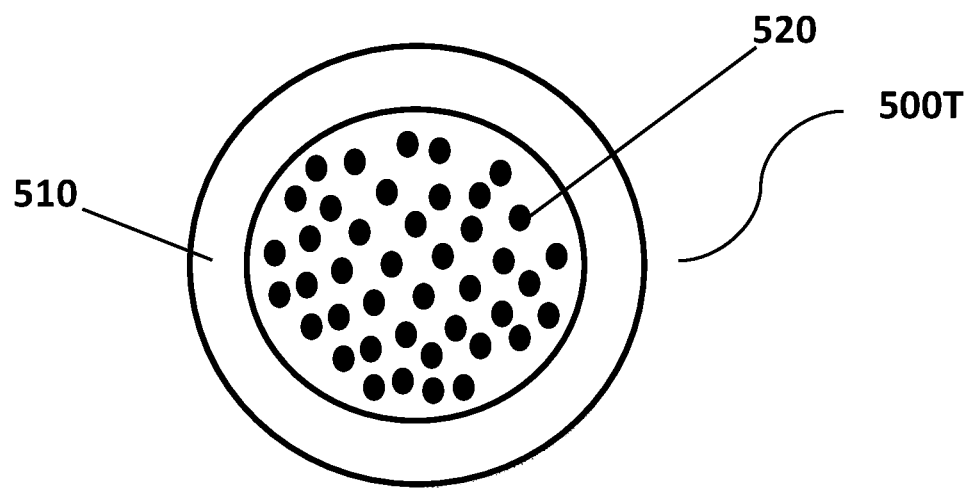
Figure 5:

FIG. 5 illustrates 3 different views of screens that may be used with apparatus consistent with the present disclosure. FIG. 5 includes a perspective view 500P, a top view 500T, and a side view 500S of a screen. Note also that the perspective view 500P and the top view 500T include edge portion 510 and holes 520 of a screen. The screen illustrated in FIG. 5 may be similar or identical to screens 300S1 and 300S2 of FIG. 3. As such, holes 520 may be smaller than dimensions associated with a size of absorptive particulate fill that may be contained within an apparatus consistent with the present disclosure. Edge portion 510 may allow the edges of a screen to be sealed when a pipe is fabricated. For example, when the portions of pipe 300 of FIG. 3 are screwed together, any vapor or smoke transferred through pipe 300 may be forced to pass through holes in the screen instead of passing around sides parts of such a screen.

Figure 6:
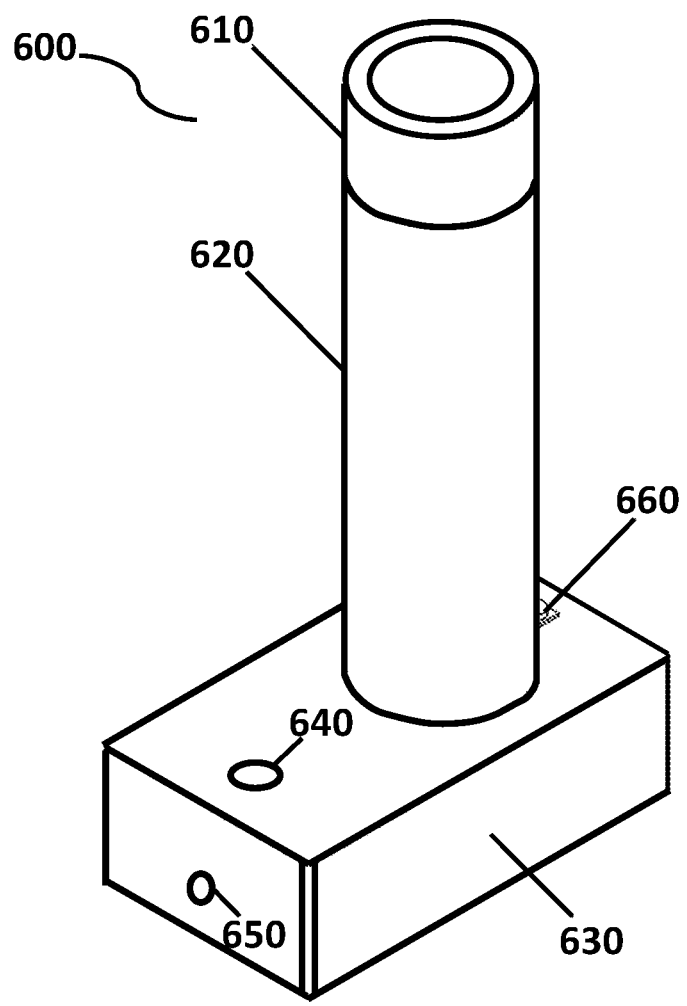
FIG. 6 illustrates a pipe consistent with the present disclosure that includes one or more electrical or electronic components.

FIG. 6 illustrates a pipe consistent with the present disclosure that includes one or more electrical or electronic components. The pipe 600 of FIG. 6 includes top portion 610, middle portion 620, and base portion 630. Base portion 630 includes hole 640, vent/clear hole 650, and switch or indicator 660. Hole 640 may be a hole like holes 160 and 360 of FIG. 1 and FIG. 3, and hole 640 may receive a bowl, a cigarette, a joint, a blunt, or a vaporizer pen when a user wishes to smoke or inhale plant materials after they have been combusted or vaporized. As such smoke or vapor from burnt *cannabis* or vaporized concentrates may be cooled and cleaned. Hole 650 may be a vent hole like vent holes 170, 270, or 370 of FIGS. 1-3. As such vent hole 650 may be covered by a user when that user inhales and may be uncovered when the user wishes to clear the pipe of smoke or vapor.

When a user wishes to inhale materials after they have been combusted or vaporized, the user may press button 660. The pressing of button 660 may cause electronics included inside of pipe 660 to be activated. In certain instances button 660 may include an indicator that includes one or more light emitting diodes and those diodes may be illuminated to indicate whether the pipe is ready to be used. In certain instances such indicators may display one or more colors, where a red indicator may inform the user to wait and a green indicator may inform the user to proceed to use pipe 600. In other instances a flashing light/LED may be used to indicate a wait state and a solid light may be used to inform the user to proceed, for example. For this or potentially other reasons, pipe 600 may be considered to be an active pipe, where pipes consistent with FIGS. 1-3 may be considered passive versions of pipes consistent with the present disclosure.

In one configuration electronics that identify whether a temperature meets or exceeds a temperature could include a temperature sensor that provides an input to a first input of voltage comparator. A second input to the comparator could be provided to a second input of the comparator. When a voltage from the temperature sensor increases to or above the threshold level, a state of the comparator could change causing a red LED to turn on when a control switch is depressed. When the voltage of the temperature sensor is below the threshold level, a green LED could be illuminated when the control switch is depressed. In such instances, an output of the comparator could be coupled to transistors, digital logic, or a timing circuit (e.g. a 555 timer) that could cause either the red or the green LED to illuminate or blink. Alternatively, electronics included in a pipe could include digital sensors, analog to digital converters, a processor and memory, or other circuits known in the art.

Figure 7:
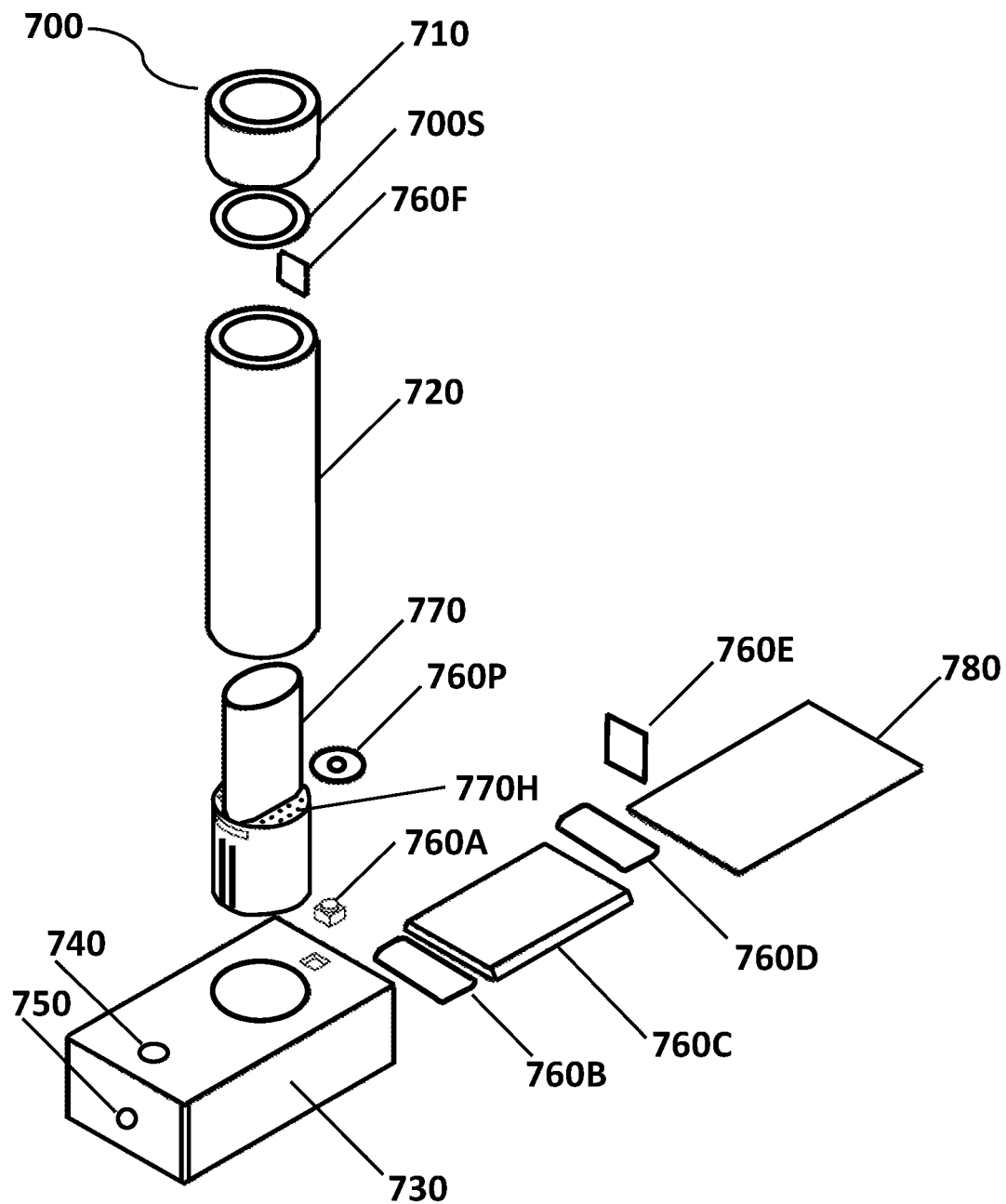
FIG. 7 illustrates components of an exemplary active apparatus consistent with the present disclosure.

FIG. 7 illustrates components of an exemplary active apparatus consistent with the present disclosure. FIG. 7 includes an upper portion 710, a middle portion 720, and a base portion 730. FIG. 7 also includes heat sink 770 that may be used to physically connect base portion 730 to middle portion 720. Top portion 710 and screen 700S may be included in apparatus 700 and these portions may be assembled in using methods discussed in respect to the portions of FIG. 3, previously discussed. Hole 740 may be a hole that receives a bowl, a cigarette, a joint, a blunt, or a vaporizer pen when a user wishes to smoke or inhale plant materials after they have been combusted or vaporized. Hole 750 may be a vent hole like vent holes 170, 270, or 370 of FIGS. 1-3. The outer portion of pipe 700 may be made of any material, materials that have greater than 50 W/m K heat transfer coefficients or materials that are more thermally isolative, such as plastic or wood. This may be the case when other cooling elements (e.g. heat sinks or thermally conductive fill) included in pipe 700 sufficiently cool heated smoke or vapors.

Electrical or electronic components included in FIG. 7 are items 760A, 760B, 760C, 760D, 760E, 760F, and 760P. Item 760A may include a switch or indicator like item 660 of FIG. 6. Items 760B, 760C, 760D, and 760E may be individual electrical or electronic components or circuit boards, where item 760C may be a battery. Items 760B, 760D, and 760E may respectively be switching transistors (e.g. bipolar or field effect transistors-MOSFET), data loggers, processors/memory, or wireless communication devices. Item 760F may be one or more sensors that sense temperature, air quality, $CO_2$ levels, or other parameters. Item 760P may be a Peltier device that is also referred to as a thermoelectric heat transfer device, a cooling module, or an electronic heat pump. In certain instances the different of electrical/electronic components illustrated in FIG. 7 may be included in a single circuit board. Most of the electrical or electronic components may be included in base portion 730. Sensor(s) 760F, however may be preferably located near or at top portion 710 such that gasses inhaled by a user can be monitored for purity, contaminates, or temperature. Item 760P may be located within heatsink 770 or may be located elsewhere in the assembly. Item 780 is a lower cover that may be attached to base portion 730 such that each of the components included in base portion 730 may be kept contained within bottom portion 730.

Holes 770H included in heat sink 770 may allow smoke, vapors, or gas to move through heat sink 770 when pipe 700 is used by a user. In such instances, control electronics 760B, 760D, and 760E may be configured to provide power from battery 760C, when a bottom side of the Peltier device 760P is heated and an upper portion of Peltier device 760P is cooled. Heated smoke or vapor passing through holes 770H may be cooled when Peltier device 760P is powered on. Upper as such Peltier device 760P can pump heat downward through the lower portion of heat sink 770 while cooling the upper portion of heat sink 770 that has the oval elongated shape in FIG. 7. The upper portion of heat sink 770 may be of any shape (e.g. round, oval, or may include fins), the upper portion of heat sink 770 may also be a tube or a round pipe. The bottom portion of heat sink 770 may be of any shape and may also include fins around which heated smoke or vapor must pass. In certain instances, the upper portion of heat sink 770 will be thermally coupled to the upper portion of Peltier device 760 via a thermal conductive medium (e.g. thermal epoxy, thermal pad, or other thermal transfer wetting agent)

An electronic module included in pipe 700 may include a processor that executes instructions out of a memory and the processor may include program code that allows pipe 700 to send data to a user device such as a cell phone, a tablet computer, or other computing device via an 802.11, a Bluetooth connection, using a proprietary wireless communication interface, or via a wired interface. In such instances, a user's user device may be configured to receive data transmitted from pipe 700 and to send that information to a doctor monitoring the use of the pipe by a patient. In such instances, program code executing at the user device may allow the user to enter information, for example data that identifies that the user filled a bowl of a predetermined size with *cannabis* plant matter or concentrate, enter a number of grams of weighed plant matter, and/or enter a potency of the *cannabis* plant matter or concentrate. When the user ignites plant matter or vaporizes an extract, the processor may receive and store sensor data that in a memory at pipe 700. This data may be transmitted to the user device and the user device may forward that data to a computing device of a doctor. Data sent for the doctor to review may include an estimate of total cannabinoids consumed by a patient using pipe 700 or raw sensor data sensed by one or more sensors. Data sent to a doctor's computer may also include information entered by the user that identifies a mass of plant matter smoked and concentrations of cannabinoids included in that smoked plant matter. Data may be sent from the pipe that was collected from or calculated by a processor at the pipe or at the user device using the collected sensor data. This sensor data may include a flow of gas, a change in pressure, or a duration of time that a Peltier device was energized. Sensor data may also include temperatures or VOCs passing through a portion of the pipe. This sensor data will allow the doctor to review an estimated number of cannabinoids consumed by the patient over time and may be used to identify that a level of VOCs or particles provided to the patent were below a critical threshold. The processor may also collect data any time the pipe is used, even when the Peltier device is not energized. For example, a rapid pressure or temperature change could cause the processor to collect data that indicates that the pipe was used without engaging the Peltier device.

Figure 8:
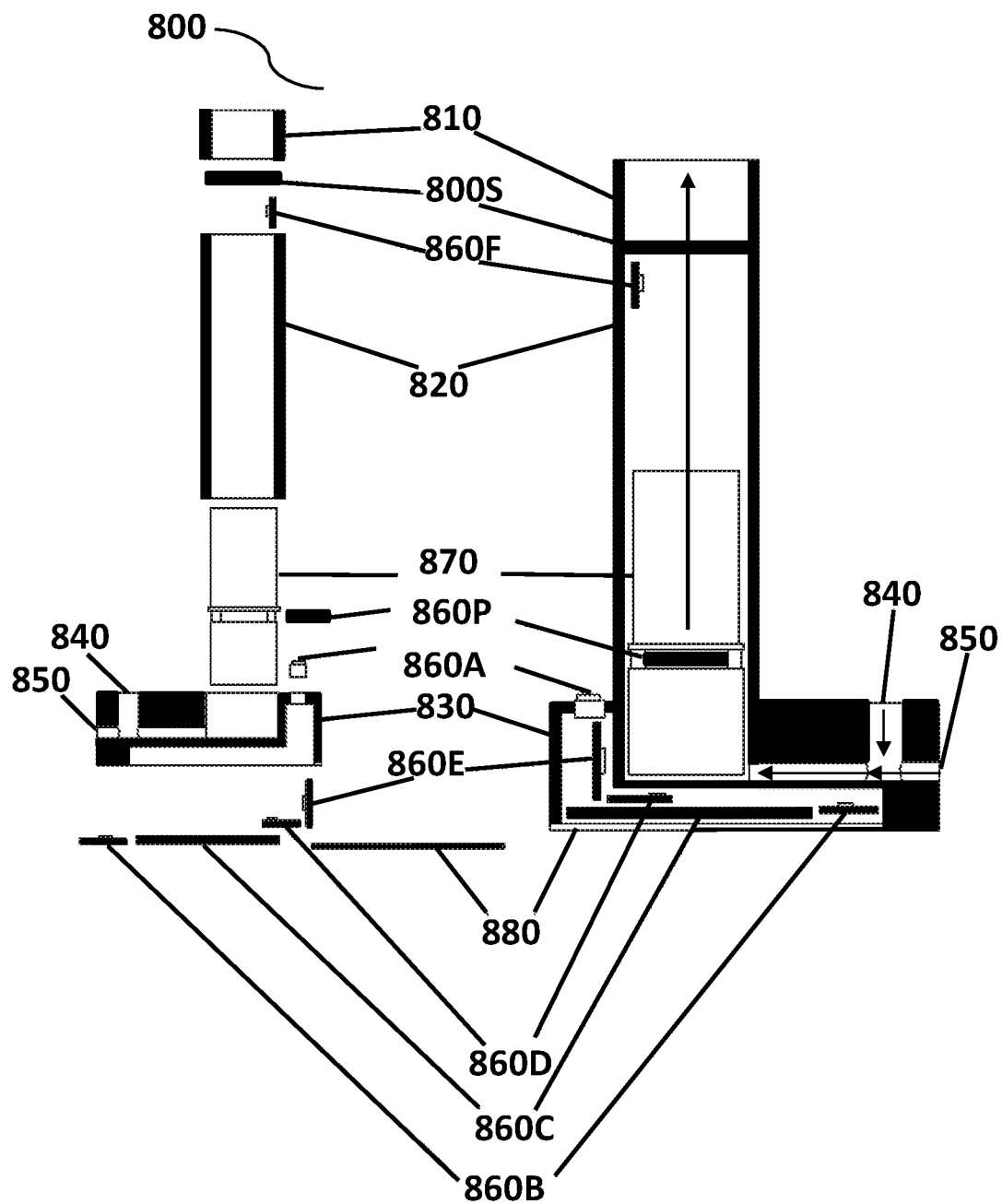
FIG. 8 illustrates semi-cross-sectional views of the apparatus shown in FIG. 7 that include left facing view (on the left side of FIG. 8) and a right facing view (on the right side of FIG. 8).

FIG. 8 illustrates semi-cross-sectional views of the apparatus shown in FIG. 7 that include left facing view (on the left side of FIG. 8) and a right facing view (on the right side of FIG. 8). FIG. 8 includes an upper portion 810, a middle portion 820, and a base portion 830. FIG. 8 also includes heat sink 870 that may be used to physically connect base portion 830 to middle portion 820. Top portion 810 and screen 800S may be included in apparatus 800 and these portions may be assembled in using methods discussed in respect to the portions of FIG. 3. Hole 840 may be a hole that receives a bowl, a cigarette, a joint, a blunt, or a vaporizer pen when a user wishes to smoke or inhale plant materials after they have been combusted or vaporized. Hole 850 may be a vent hole like vent holes 170, 270, or 370 of FIGS. 1-3.

Electrical or electronic components included in FIG. 8 are items 860A, 860B, 860C, 860D, 860E, 860F, and 860P. Item 860A may be a switch or indicator like the switch or indicator 660 of FIG. 6. Items 860B, 860C, 860D, and 860E may be individual electrical or electronic components or circuit boards, where item 860C may be a battery. Items 860B, 860D, and 860E may respectively be switching transistors (e.g. bipolar or field effect transistors-MOSFET), data loggers, processors/memory, or wireless communication devices. Item 860F may be one or more sensors that sense temperature, pressure, air quality, $CO_2$ levels, or other parameters. Item 860P may be a Peltier cooler that is also referred to as a thermoelectric heat pump. In certain instances the different pieces of electrical/electronic components may be included in fewer assemblies than illustrated in FIG. 8. Most of the electrical or electronic components may be included in base portion 830. Sensor(s) 860F, however may be preferably located near or at top portion 810 such that gasses inhaled by a user can be monitored for purity, contaminates, or temperature. Item 860P may be located within heatsink 870 or may be located elsewhere in the assembly. Item 880 is a lower cover that may be attached to base portion 830 such that each of the components included in base portion 830 may be kept contained within bottom portion 830.

Note that the semi-cross-sectional views included in FIG. 8 show locations where components may be included within apparatus 800 of FIG. 8. Note that the semi-cross-sectional view located on the right side of FIG. 8 includes all of the electrical or electronic components contained within different areas of apparatus 800. The arrows included in FIG. 8 illustrate pathways through which smoke or gasses may be sucked through pipe 800, when a user inhale components after those components have been combusted or vaporized. Note that smoke or gasses may move through hole 840 or hole 850 and then through heat sink 870 (via holes or fins of heat sink 870), middle portion 820, and top portion 810 based on suction provided by a user sucking on upper portion 810 of pipe 800.

Figure 9:
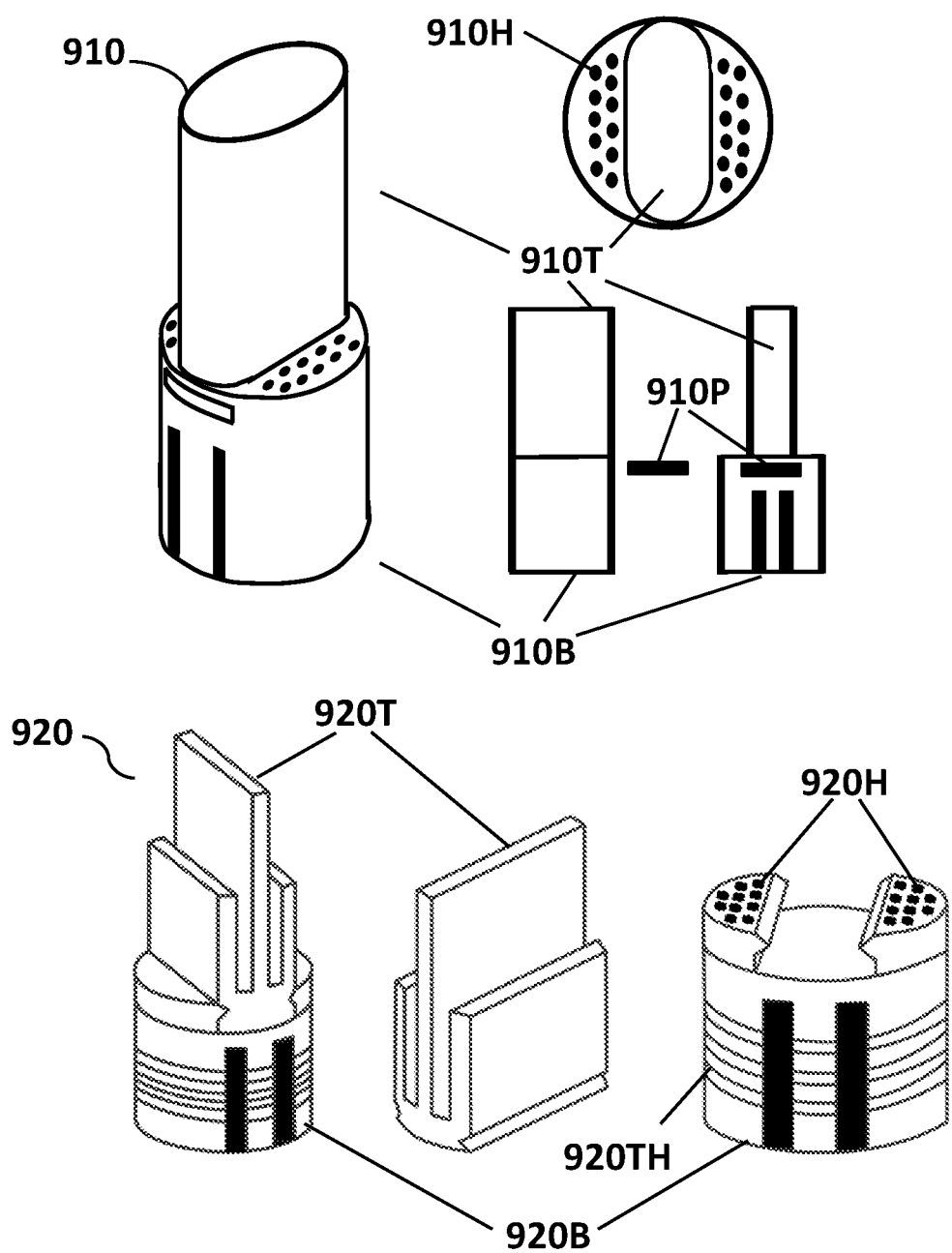
FIG. 9 illustrates two different heat sink devices that may be used in apparatus consistent with the present disclosure.

FIG. 9 illustrates two different heat sink devices that may be used in apparatus consistent with the present disclosure. FIG. 9 includes a first heat sink 910 and a second heat sink 920 that have slightly different shapes. Heat sink 910 includes top portion 910T and bottom portion 910B that in certain instances may have been made as separate pieces that fit together. Heat sink 910 also includes a Peltier thermoelectric device 910P that may fit between top portion 910T and bottom portion 910B of heat sink 910. Holes 910H in heat sink heat sink 910 may provide a pathway for heated gasses, smoke, or vapor to pass through as those gasses, smoke, or vapor are actively cooled by operation of thermoelectric device 910P.

Heat sink 920 includes top portion 920T and bottom portion 920B that may be disassembled or assembled by sliding top portion 920T into a notch included in bottom portion 920B. Heat sink 920 also includes holes 920H through which gas, smoke, or vapor may be drawn when heat sink 920 is assembled into a pipe. Note that the bottom portion 920B of heat sink 920 includes threads 920TH that may be used to screw heat sink 920 into a base portion of a pipe.

Figure 10:
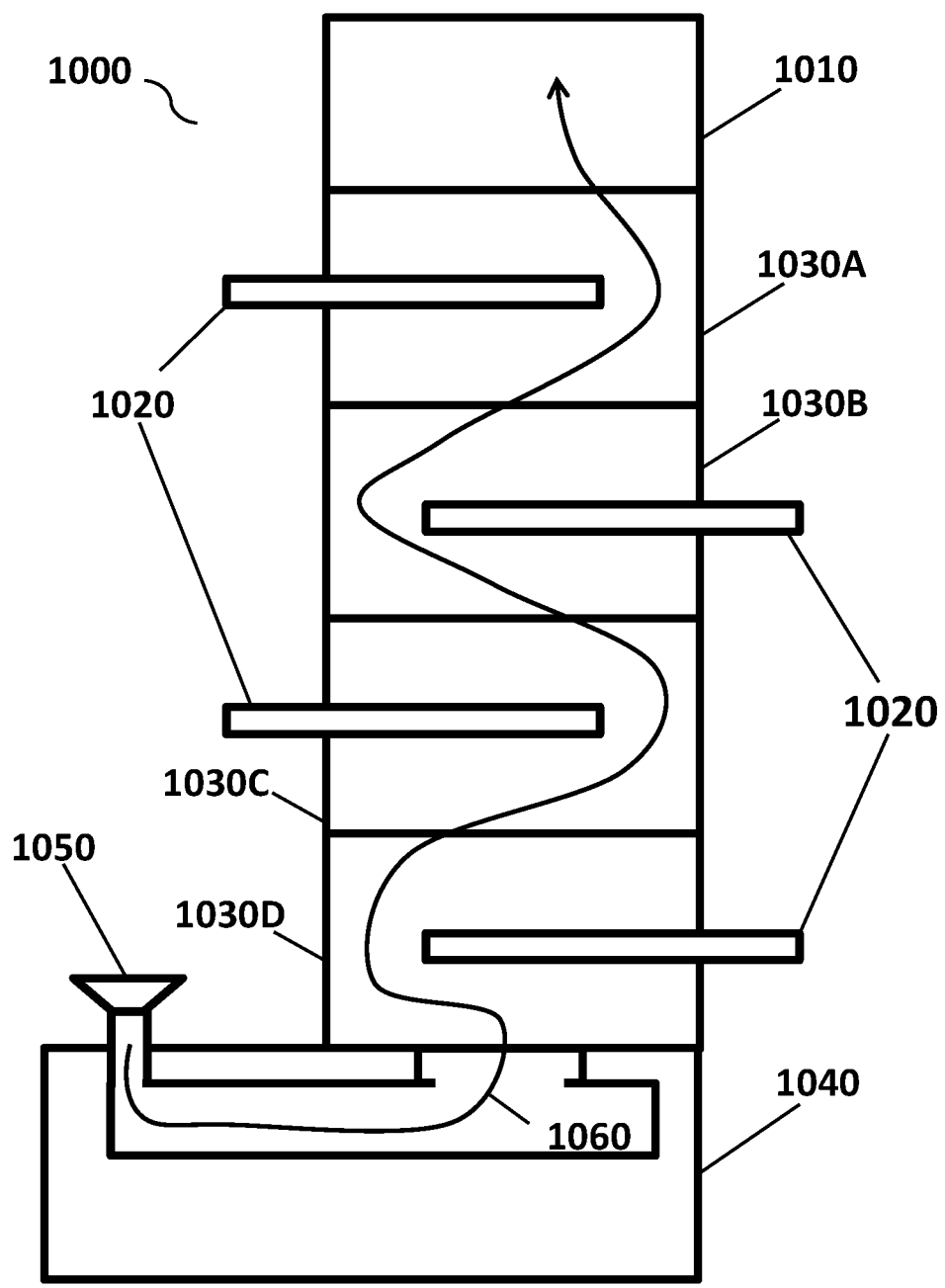
FIG. 10 illustrates an apparatus consistent with the present disclosure that includes multiple different chambers.

FIG. 10 illustrates an apparatus consistent with the present disclosure that includes multiple different chambers. The apparatus or pipe 1000 of FIG. 10 includes a top portion 1010, heat sinks 1020, chambers 1030A-1030C (1030A, 1030B, 1030C, and 1030D), base portion 1040, and bowl 1050. When plant matter is ignited in bowl 1050 as a person sucks on top portion 1010 of pipe 1000, smoke 1060 may be drawn along the path illustrated by the meandering arrowed line. Not that smoke 1060 moves from pipe 1050 through a channel in base portion 1040 and through each of the chambers 1030A-1030D before exiting pipe 1000 through top portion 1010.

Heat sinks 1020 may be wedge shaped flat pieces made of heat conductive materials that transfer heat from internal portions of pipe 1000 to outside surfaces of pipe 1000. Each of the different chambers 1030A-1030D may contain one or more different materials that transfer heat or that absorb or chemically neutralize VOCs (e.g carbon monoxide (CO) or dioxide ($CO_2$)). Chamber 1030A-1030D may also be separated by one or more screens like screens 300S1 and 300S2 of FIG. 3 or the screen illustrated in FIG. 5. In certain instances, each separate chamber may include a different material fill or may include material fills of different sizes. For example, chamber 1030D may include a set of heat absorbing beads of a first diameter, chamber 1030C may include a second set of heat absorbing beads of a second diameter, chamber 1030B may include flakes of a first size of materials that absorb $CO_2$, and chamber 1030A may include flakes of a material that absorbs heat.

Apparatus consistent with the present disclosure may include cooling or filtering elements that have dimensions that are greater than a dimension of a material that is burnt or vaporized. A volume of fill in one or more chambers that smoke must travel through may be larger than a volume of plant material burned when a person fills their lungs with smoke from the burnt volume of plant matter. Fill material may be characterized by a measure of impedance and a capacity to absorb heat. Fill material may also be characterized by the fill materials ability to filter particles or VOCs. Preferred fill materials may be identified by a process that evaluates sensor data or by scientific analysis that may include the use of an analytic tester (high or ultra-performance liquid chromatograph tester, gas chromatograph tester, other spectral tester, or other testers). An impedance of fill material may be characterized using pressure sensors or flow sensors at an input and at an output of a pipe as smoke is drawn through the pipe that contains a known volume of fill material. As such apparatus consistent with the present disclosure may include fill that provides less than a threshold impedance to the flow of gas, smoke, or vapor through a volume of the fill material that is located in one or more chambers of the apparatus. A volume of fill included in such apparatus may also provide ability to remove more than a threshold percentage of VOCs or particulate materials as verified by laboratory or sensor tests. Furthermore, heat sinks consistent with the present disclosure may direct the flow of gas around hard surfaces of one or more heat sinks (e.g. heat sinks of 130, 230, 330, 770, 870, 910, 920, 1020, 1120 of FIGS. 1-3 & 7-11). Heat sinks may force the flow of smoke or vapor through a desired route that increases contact with outer surfaces of fill or that increases the length of a path that the smoke or vapor must pass through when the smoke or vapor passes through an apparatus consistent with the present disclosure.

A volume of cooling material through which smoke or vapor must pass that is greater than a volume of material that is burned when a person inhales a lung full of cooled and filtered smoke may be characteristic of a pipe consistent with the present disclosure. The greater length and or width along a route that the smoke or vapor must pass may provide an enhanced cooling and filtering effect. Alternatively or additionally as reviewed above, apparatus consistent with the present device may include an active cooling device, such as a Peltier heat transfer device.

Figure 11:
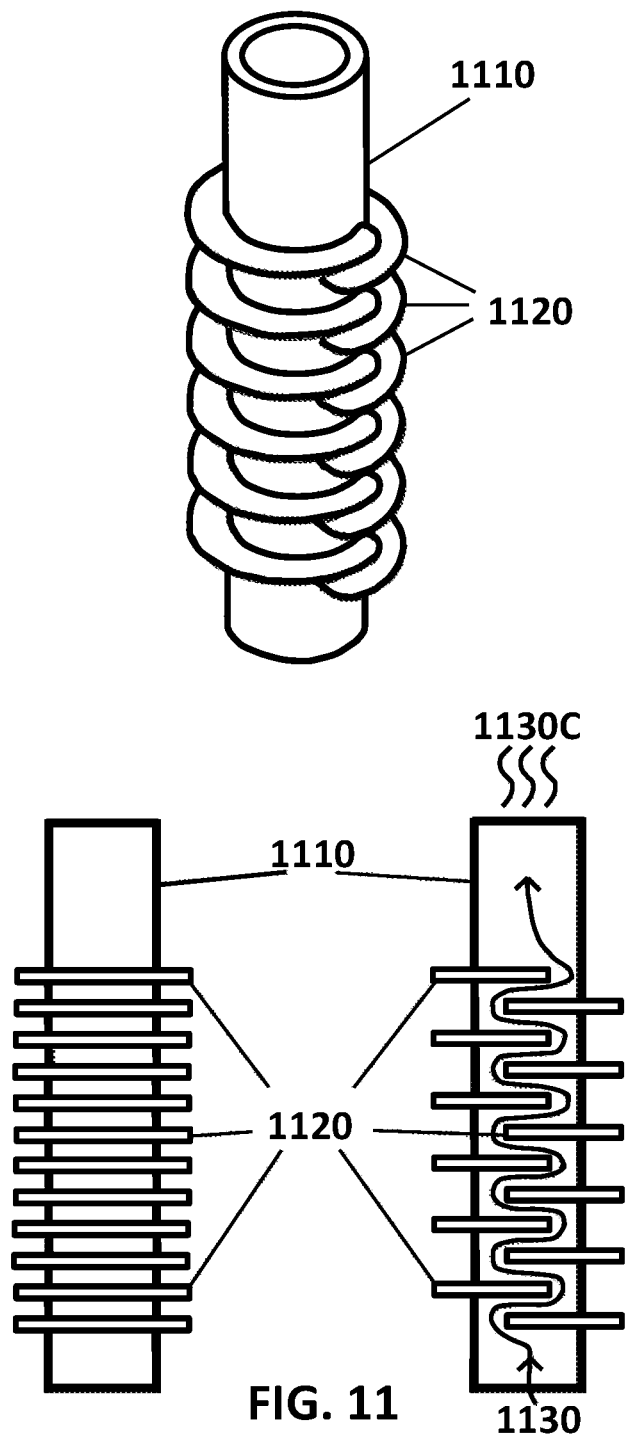
FIG. 11 illustrates a tube that may be a used to cool heated gasses, smoke, or vapor when a person inhales gasses or vapors consistent with the present disclosure.

FIG. 11 illustrates a tube that may be a used to cool heated gasses, smoke, or vapor when a person inhales gasses or vapors consistent with the present disclosure. FIG. 11 includes a perspective view and two different side views of a smoking apparatus consistent with the present disclosure. Note that each of these different views include cylindrical portion 1110 and heat sinks 1120. The heat sinks 1120 of FIG. 11 may be shaped, as such they may be made to have semi-circular shapes or spiral shapes. Heated gasses, smoke, or vapor 1130 are illustrated as passing through the lower right cylinder 1110 of FIG. 11 via a meandering path indicated by the arrowed line 1130 in FIG. 11. As the gas, smoke, or vapor moves through cylinder 1110, it may encounter heat sinks 1120 as it is cooled before exiting cylinder 1110 as cooled gas, smoke, or vapor 1130C. Here again cylinder 1110 may be filled with one or more different types of heat or VOC absorbing material fills.

The apparatus of FIG. 11 may be attached to a base portion, such as base portion 150, 250, 350, 630, 730, 830, 1040 of FIGS. 1, 2, 3, 6, 7, 8, and 10 respectively. The apparatus of FIG. 11 may also include other heat sinks, heat transfer materials, or thermoelectric devices discussed in this disclosure. As such, heat sink 770 of FIG. 7, 870 of FIG. 8, 910 or 920 of FIG. 9 may be incorporated into the apparatus of FIG. 11. Alternatively or additionally, the apparatus of FIG. 11 may include thermoelectric devices similar to 760P of FIG. 7, 860P of FIG. 8, or 910P of FIG. 9.

In certain instances, the apparatus of FIG. 11 may be an inline device similar to a cigarette holder where a smoke-able material contained within a paper cover may be inserted in one end of cylinder 1110 when a person inhales on a second end of cylinder 1110. For example, a cigarette or vaporizer pen may be inserted into cylinder 1110 such that the person may inhale cooled gasses, smoke, or vapor.

Figure 12:
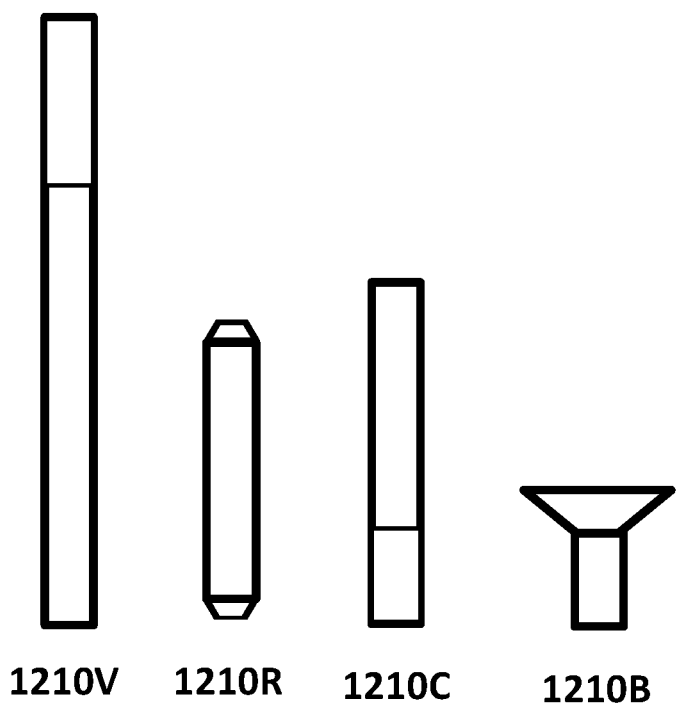
FIG. 12 illustrates several different types of items that may be inserted into a hole of an apparatus consistent with the present disclosure.

FIG. 12 illustrates several different types of items that may be inserted into a hole of an apparatus consistent with the present disclosure. FIG. 12 illustrates vaporizer pen 1210V, a rolled (cigarette, joint, or blunt) 1210R, a cigarette 1210C, or a bowl 1210B. As such, apparatus consistent with the present disclosure may be used by a person to receive existing devices to allow users to inhale tobacco, *cannabis*, hashish, nicotine concentrates, *cannabis* concentrates, or other materials at cooler temperatures as compared to what is possible with using smoking or vaporizer apparatus as they were originally intended to be used.

Figure 13:
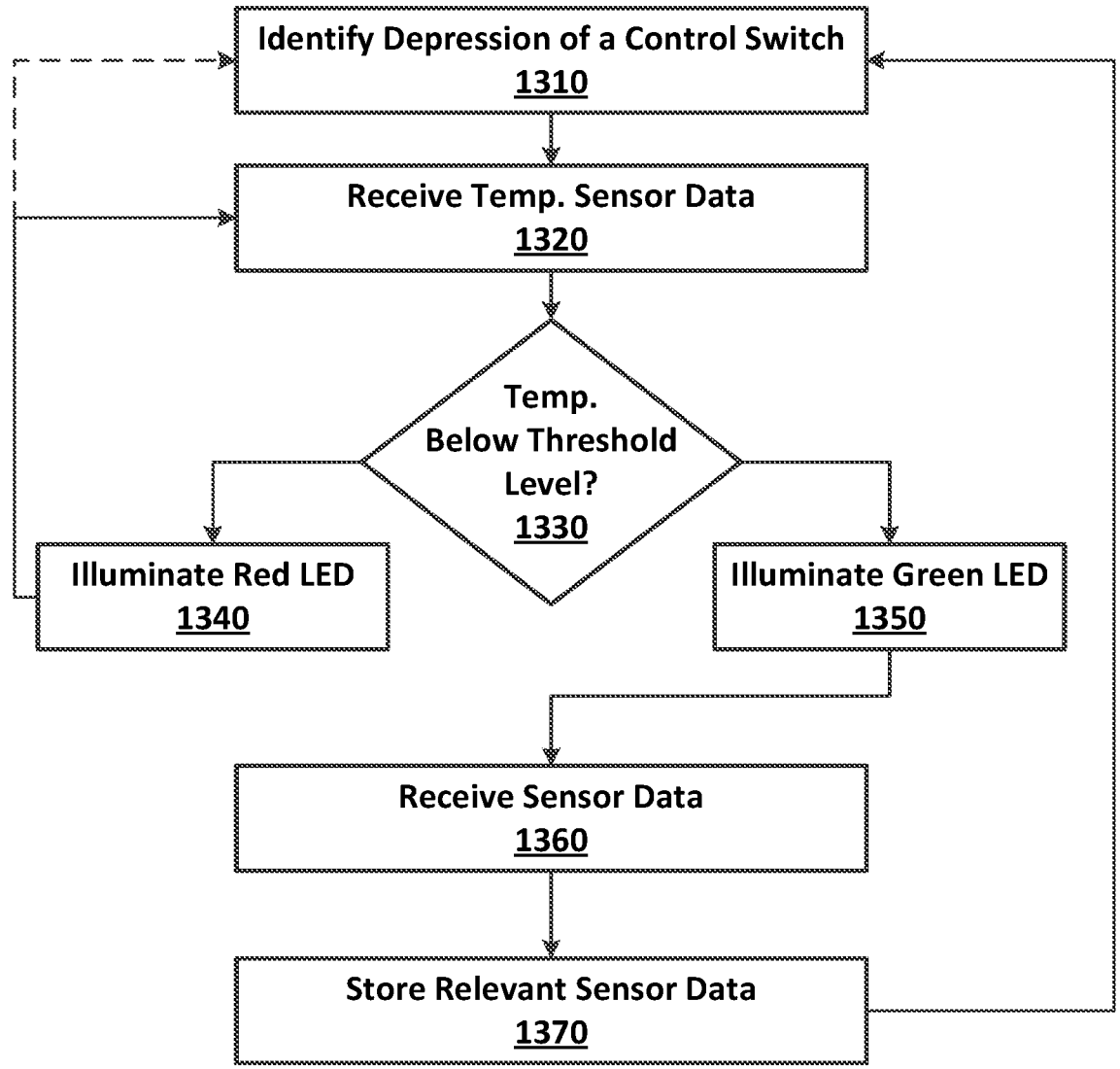
FIG. 13 illustrates a series of steps that may be performed by a control system consistent with the present disclosure.

FIG. 13 illustrates a series of steps that may be performed by a control system consistent with the present disclosure. Before a user depresses a control switch, the user may fill a bowl of a pipe with *cannabis*. In certain instances, the user may first weigh the *cannabis* put into the bowl or the bowl may be of a size that when filled should contain a known mass of *cannabis* plant matter. In certain instances, the plant matter in the bowl may contain a known mass of cannabinoids based on a known concentration of cannabinoids per gram of cannabinoids. For example, when plant matter includes 20% THC by mass, a gram of that plant matter should contain 20 milligrams (mg) of THC. When a person smokes about 0.5 grams of such plant matter, they will consume about 10 mg of THC.

After the bowl has been filled the user may depress a control switch, and a control system may then identify that the control switch has been depressed in step 1310 of FIG. 3. Next the control system may receive data from a temperature sensor in step 1320. Determination step 1330 may the identify whether identify that a temperature is below a threshold level, when no program flow may move to step 1340 where a red light emitting diode (LED), other indicator may be illuminated (flashed), or information may be displayed on a display indicating that the temperature is at or above the threshold level. In certain instances, indicators may include audio tones or words emitted by a speaker or audio output device. After step 1340 program flow may move back to step 1320 where temperature sensor data is again received. While not illustrated in FIG. 13, program flow could alternatively move from step 1340 to step 1310 as indicated by the dashed line of FIG. 13. In instances when a Peltier device is used to cool smoke or vapor and the battery at the pipe has been discharged below a threshold level, the pipe may still have the ability to cool smoke or vapor. If however, when battery voltage is low and the temperature of smoke or vapor increases above a threshold level, a warning may be provided via an LED or other indicator (e.g. a display or audio output device). This may allow a user to place the pipe in a refrigerator to cool the pipe so it can be used after a few minutes.

In instances when the temperature is identified to be below the threshold level in step 1330, program flow may move to step 1350 where a green LED or other indicator (display or audio output device) may be presented to the user. The green LED or other indicator may identify that the temperature is in a preferred range for smoking. The user may then ignite the plant matter and suck on a pipe output when inhaling combusted materials. Additional sensor data may be then be received in step 1360 of FIG. 3, this additional sensor data may be received from one or more different types of sensors. Types of sensors that may be included in an apparatus consistent with the present disclosure may include one or more of the temperature sensor, a carbon dioxide ($CO_2$), a carbon monoxide sensor (CO), other VOC sensors, a particle sensor, a pressure sensor, or a flow sensor. In certain instances two pressure sensors, one located near an input of a pipe and the other located near the output of the pipe may sense pressures when a processor monitors a pressure change or flow through the pipe. Flow sensors could also allow the processor to measure a flow or a volume of gas, smoke, or vapor that passes through the pipe. After step 1360, any relevant sensor data may be stored in memory for later evaluation in step 1370 of FIG. 13. Here again usage data may be sent to a computer on the Internet or to a computer of a doctor and this data may be routed through a user device, such as a cell phone or other computing device. After step 1370, program flow may move back to step 1310 of FIG. 13.

In certain instances, repeated use of a pipe may cause temperatures at a pipe output to increase to or above the threshold level. This may cause a warning indicator to illuminate, informing the user that the output temperature has increased. The steps illustrated in FIG. 13 may be performed by a control system in a pipe that uses active cooling devices (like a thermo-electric heat transfer device) or that use passive cooling mechanisms. While not illustrated in FIG. 13 output indicators may also be used to inform a user of current levels of $CO_2$, CO, or other VOCs via a display, audio indication, or by blinking patterns of a LED. Levels of $CO_2$, CO, or other VOCs that cause an indication to be provided may be set automatically, may have been set by a user, or may have been set by a doctor. Such settings may be received via a wireless communication interface from a user device.

Pressure sensor data or flow sensor data may be used to identify or approximate a number of milligrams of a cannabinoid that has been inhaled by a user and this milligram data may be stored in a persistent memory for later access and evaluation. Apparatus consistent with the present disclosure may thus be used to identify approximate milligram dosages of cannabinoids that have been consumed by the user over time.

Electronics included inside of a smoking apparatus may also include a processor, a memory, and a wireless communication (e.g. a 802.11, Bluetooth, or other) interface. The processor may collect sensor data and then send that data via the wireless interface to a user computing device, such as a cell phone, tablet computer, or other computing device. In certain instances the processor executing instructions out of the memory may perform calculations that convert raw sensor data into consumption data. This consumption data may identify an estimated number of milligrams of cannabinoids consumed by a person during a smoking session. The electronics at the smoking apparatus may communicate either raw sensor data or consumption data to a user device and the user device may be configured to communicate via an application program or a web interface with a website or with a computing device of a doctor. In instances when the user device receives raw sensor data from the smoking apparatus, the execution of program code at the user device may perform calculations to convert the sensor data into consumption data. Alternatively raw sensor data could be sent to a website or to the doctor's computer where the sensor data could be converted into consumption data. In certain instances, a user device may download an application program from a website such as the Apple store.

Figure 14:
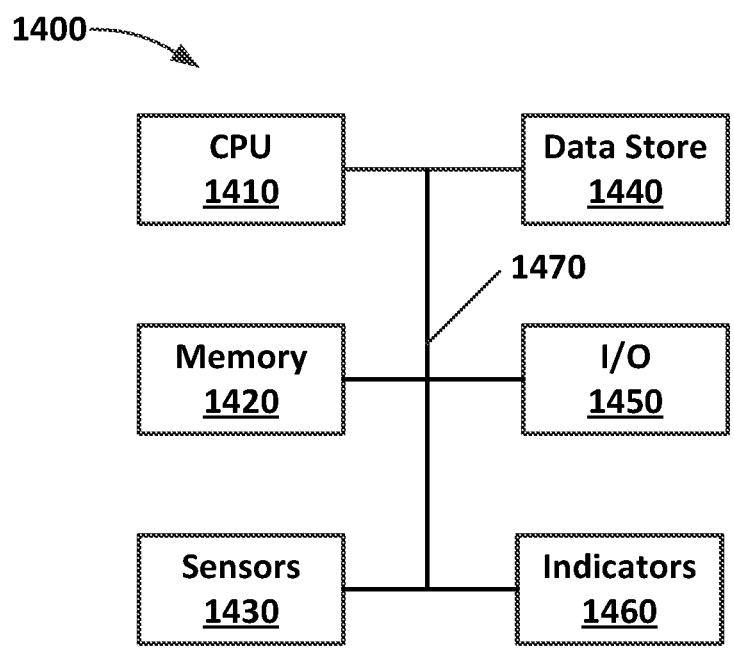
FIG. 14 illustrates a control system that may be used with an apparatus consistent with the present disclosure.

FIG. 14 illustrates a control system that may be used with an apparatus consistent with the present disclosure. Control system 1400 of FIG. 14 includes CPU 1410, memory 1420, sensors 1430, data store 1440, inputs/outputs (I/O) 1450, and indicators (e.g. LEDs, a display, or audio output) that are connected to each other via communication bus 1470. CPU 1410 may include one or more processors that execute instructions out of memory 1420. Data store 1440 may be a non-volatile form of memory, such as a flash memory device or disk drive. I/O 1450 may include one or more different types input or output devices including, yet not limited to a network interface (wired or wireless), interfaces that can connect to additional sensors or other devices (e.g. an expansion bus like USB), an audio interface (speaker, microphone, piezoelectric device), or a touch screen/pad. Indicators 1460 may be a display that may include a graphical user interface (GUI) or may include or be comprised of one or more light emitting diodes (LEDs). Input devices 1450 may provide a receive user input. As such, input devices 1450 may include an alpha-numeric keypad (e.g. a keyboard for inputting alpha-numeric and other information) or be a pointing device (e.g. a mouse, a trackball, stylus, or cursor direction keys). In certain instances, different sized smoking bowls may be associated with different milligram dosages of a cannabinoid consumed by a person.

The components shown in FIG. 14 are depicted as being connected via a single bus 1470. However, the components may be connected through one or more data transport means. For example, CPU 1410 and memory 1420 may be connected via a local microprocessor bus, and the storage device 1440, I/O device(s) 1450, and indicators 1460 may be connected via one or more input/output (I/O) buses. Apparatus consistent with the present disclosure may be configured to send messages to a computing device whenever a smoking apparatus is used. This could enable an owner of the pipe to identify that the pipe was used by another person. In an instance when the pipe is located at the home of an owner and the owner is away from home, a computer at the home could receive a wireless transmission indicating that the pipe has been used. This could cause a message to be texted to a cell phone of the user. An APP operating at the cell phone could then generate an alarm based on a settings set in the APP. For example, the owner could identify that pipe use during certain times of day (e.g. between 8 am and 5 pm) that should cause an audio alarm to be generated. Alarm conditions could also be generated when the pipe is used when the owner's phone is located at a different global positioning location (GPS) than a home or other specified location where the pipe currently resides. Such messages and alarms could allow a parent to guarantee that their child (or other person) have not used their pipe or to identify that their child (or other person) has used their pipe inappropriately.

The components contained in the controls system 1400 of FIG. 14 may be like those that are typically found in computer systems or computer modules that may be suitable for use with embodiments of the present invention and are intended to represent a broad category of such computer components that are well known in the art. Thus, the computer system 1400 of FIG. 14 can be a personal computer, a hand held computing device, a telephone ("smart" or otherwise), a mobile computing device, a workstation, a server (on a server rack or otherwise), a minicomputer, a mainframe computer, a tablet computing device, a wearable device (such as a watch, a ring, a pair of glasses, or another type of jewelry/clothing/accessory), a video game console (portable or otherwise), an e-book reader, a media player device (portable or otherwise), a vehicle-based computer, some combination thereof, or any other computing device. The computer can also include different bus configurations, networked platforms, multi-processor platforms, etc. The computer system 1400 may in some cases be a virtual computer system executed by another computer system. Various operating systems can be used including Unix, Linux, Windows, Macintosh OS, Palm OS, Android, iOS, and other suitable operating systems. When computer system 1400 is a server or doctor computer that receives usage information for a patient, program code at computer 1400 may compare usage data with prescribed milligram dosages or with other metrics of interest to a doctor.

Alternatively or additionally, controls systems consistent with the present disclosure may include or consist of analog components (e.g. comparators, voltage divider references, or transistors), discrete logic, field programmable gate arrays (FPGA), application specific integrated circuits (ASAC), or may include one or more electronic modules that are commercially purchased and configured to implement methods consistent with the present disclosure.

The present invention may be implemented in an application that may be operable using a variety of devices. Non-transitory computer-readable storage media refer to any medium or media that participate in providing instructions to a central processing unit (CPU) for execution. Such media can take many forms, including, but not limited to, nonvolatile and volatile media such as optical or magnetic disks and dynamic memory, respectively. Common forms of non-transitory computer-readable media include, for example, FLASH memory, a flexible disk, a hard disk, magnetic tape, any other magnetic medium, a CD-ROM disk, digital video disk (DVD), any other optical medium, RAM, PROM, EPROM, a FLASH EPROM, and any other memory chip or cartridge.

The present invention may be implemented in an application that may be operable using a variety of devices. Non-transitory computer-readable storage media refer to any medium or media that participate in providing instructions to a central processing unit (CPU) for execution. Such media can take many forms, including, but not limited to, non-volatile and volatile media such as optical or magnetic disks and dynamic memory, respectively. Common forms of non-transitory computer-readable media include, for example, a floppy disk, a flexible disk, a hard disk, magnetic tape, any other magnetic medium, a CD-ROM disk, digital video disk (DVD), any other optical medium, RAM, PROM, EPROM, a FLASH EPROM, and any other memory chip or cartridge.

While various flow diagrams provided and described above may show a particular order of operations performed by certain embodiments of the invention, it should be understood that such order is exemplary (e.g., alternative embodiments can perform the operations in a different order, combine certain operations, overlap certain operations, etc.).

The foregoing detailed description of the technology herein has been presented for purposes of illustration and description. It is not intended to be exhaustive or to limit the technology to the precise form disclosed. Many modifications and variations are possible in light of the above teaching. The described embodiments were chosen in order to best explain the principles of the technology and its practical application to thereby enable others skilled in the art to best utilize the technology in various embodiments and with various modifications as are suited to the particular use contemplated. It is intended that the scope of the technology be defined by the claim.

What is claimed is:

1. An apparatus for cooling heated smoke or vapor for inhalation, the apparatus comprising:
   a housing defining at least one chamber, the housing having a first end portion and a second end portion;
   the first end portion of the housing defining an input configured to receive the heated smoke or vapor, wherein the input opens into the at least one chamber in the housing;
   a heat transfer material other than water located in the at least one chamber in the housing and configured to cool the heated smoke or vapor as it passes through the at least one chamber in the housing, wherein the heat transfer material is a solid at room temperature, the heat transfer material comprising spaced apart heat transfer elements; and
   the second end portion of the housing defining an output configured to release the cooled smoke or vapor for being inhaled by a subject.

2. The apparatus of claim 1, wherein the heat transfer material has a thermal conductivity greater than 50 Watts per meter Kelvin (W/m*K).

3. The apparatus of claim 1, wherein the heat transfer material comprises a heat sink and the heat sink comprises at least one of aluminum, copper, gold, silver, stainless steel, graphite, carbon, or carbon nanotubes.

4. The apparatus of claim 1, wherein the at least one chamber has an inner surface, and wherein the heat transfer material projects from the inner surface of the at least one chamber to an internal volume of the at least one chamber.

5. The apparatus of claim 1, wherein the at least one chamber has an outer surface, and wherein the heat transfer material projects from an internal volume of the at least one chamber to the outer surface of the at least one chamber.

6. The apparatus of claim 1, further comprising an adsorptive fill in the at least one chamber.

7. The apparatus of claim 6, wherein the adsorptive fill is in an intermediate portion of the housing adjacent the heat transfer material, wherein the intermediate portion is between the first end portion and the second end portion.

8. The apparatus of claim 6, wherein the heat transfer material is in a first chamber and the adsorptive fill is in a second chamber, and wherein the first chamber communicates with the second chamber.

9. The apparatus of claim 7, wherein the adsorptive fill comprises at least one of graphite beads, graphite flakes, carbon beads, carbon flakes, charcoal beads, charcoal flakes, activated carbon, activated charcoal, or a rock or mineral that chemically binds with carbon dioxide.

10. The apparatus of claim 6, further comprising a screen located between the first chamber and the output, wherein the screen comprises openings smaller than a smallest dimension of the adsorptive fill.

11. The apparatus of claim 1, further comprising:
    a thermoelectric heat transfer device thermally coupled to the heat transfer material; and
    a battery electrically coupled to the thermoelectric heat transfer device.

12. The apparatus of claim 1, further comprising:
    a sensor configured to measure at least one of temperature, purity, or contamination level of the cooled smoke or vapor, wherein the sensor is between the heat transfer material and the output;
    an indicator; and
    a processor configured to activate the indicator when at least one of the temperature, the purity, or the contamination level of the cooled smoke or vapor has met or exceeded a threshold temperature, threshold purity level, or threshold contamination level to indicate that the apparatus is not ready for use.

13. The apparatus of claim 12, wherein the sensor is configured to measure the temperature of the cooled smoke or vapor.

14. The apparatus of claim 1, further comprising:
    a sensor configured to measure at least one of temperature, purity, or contamination level of the cooled smoked or vapor, wherein the sensor is between the heat transfer material and the output;
    an indicator; and
    a processor configured to activate the indicator when at least one of the temperature, the purity, or the contamination level of the cooled smoke or vapor is below a threshold temperature, threshold purity level, or threshold contamination level to indicate that the apparatus is ready for use.

15. A method for cooling heated smoke or vapor for inhalation, the method comprising:
    providing a smoking apparatus comprising:
        a housing defining at least one chamber, the housing having a first end portion and a second end portion;
        the first end portion of the housing defining an input configured to receive the heated smoke or vapor, wherein the input opens into the at least one chamber in the housing;
        a heat transfer material other than water located in the at least one chamber in the housing and configured to cool the heated smoke or vapor as it passes through the at least one chamber in the housing, wherein the heat transfer material is a solid at room temperature, the heat transfer material comprising spaced apart heat transfer elements;
        and the second end portion of the housing defining an output configured to release the cooled smoke or vapor;
    releasing the heated smoke or vapor into the first end portion of the smoking apparatus; and cooling the heated smoke or vapor by allowing it to pass through the at least one chamber in the housing and over the heat transfer material.

16. The method of claim 15, further comprising:
measuring the temperature of the cooled smoke or vapor by a temperature sensor;
comparing the temperature measured by the temperature sensor with a reference that corresponds to a threshold temperature; and
if the temperature of the cooled smoke or vapor is at or below the threshold temperature, activating a first indicator.

17. The method of claim 16, further comprising activating a second indicator if the temperature of the cooled smoke or vapor is above the threshold temperature.

18. The method of claim 15, further comprising:
measuring the temperature of the cooled smoke or vapor by a temperature sensor;
comparing the temperature measured by the temperature sensor with a reference that corresponds to a threshold temperature; and
if the temperature of the cooled smoke or vapor is above the threshold temperature, activating a first indicator.

19. A method for cooling heated smoke or vapor for inhalation, the method comprising:
providing a smoking apparatus comprising:
a housing defining at least one chamber, the housing having a first end portion and a second end portion;
the first end portion of the housing defining an input configured to receive the heated smoke or vapor, wherein the input opens into the at least one chamber in the housing;
a heat transfer material other than water located in the at least one chamber in the housing and configured to cool the heated smoke or vapor as it passes through the at least one chamber in the housing, wherein the heat transfer material is a solid at room temperature;
and the second end portion of the housing defining an output configured to release the cooled smoke or vapor;
releasing the heated smoke or vapor into the first end portion of the smoking apparatus; and
cooling the heated smoke or vapor by allowing it to pass through the at least one chamber in the housing and over the heat transfer material; and
sending a communication to an external electronic device via a communication interface, wherein the communication transmits data obtained by a sensor on the smoking apparatus.

20. An apparatus for cooling heated smoke or vapor for inhalation, the apparatus comprising:
a housing defining at least one chamber, the housing having a first end portion and a second end portion;
the first end portion of the housing defining an input configured to receive the heated smoke or vapor, wherein the input opens into the at least one chamber;
a heat transfer material located in the at least one chamber configured to cool the heated smoke or vapor as it passes through the at least one chamber, wherein the heat transfer material is a solid at room temperature; and
the second end portion of the housing defining an output configured to release the cooled smoke or vapor for being inhaled by a subject;
wherein the at least one chamber has an inner surface, and wherein the heat transfer material projects from the inner surface of the at least one chamber to an internal volume of the at least one chamber.

21. An apparatus for cooling heated smoke or vapor for inhalation, the apparatus comprising:
a housing defining at least one chamber, the housing having a first end portion and a second end portion;
the first end portion of the housing defining an input configured to receive the heated smoke or vapor, wherein the input opens into the at least one chamber in the housing;
a heat transfer material other than water located in the at least one chamber in the housing and configured to cool the heated smoke or vapor as it passes through the at least one chamber in the housing, wherein the heat transfer material is a solid at room temperature;
the second end portion of the housing defining an output configured to release the cooled smoke or vapor for being inhaled by a subject; and
at least one screen disposed in the housing and configured to hold an adsorptive fill in the housing.

22. An apparatus for cooling heated smoke or vapor for inhalation, the apparatus comprising:
a housing defining at least one chamber, the housing having a first end portion and a second end portion;
the first end portion of the housing defining an input configured to receive the heated smoke or vapor, wherein the input opens into the at least one chamber in the housing;
an adsorptive fill in the at least one chamber, the adsorptive fill comprising at least one of graphite beads, graphite flakes, carbon beads, carbon flakes, charcoal beads, charcoal flakes, activated carbon, activated charcoal, or a rock or mineral that chemically binds with carbon dioxide; and
the second end portion of the housing defining an output configured to release the cooled smoke or vapor for being inhaled by a subject.

23. An apparatus for cooling heated smoke or vapor for inhalation, the apparatus comprising:
a housing defining at least one chamber, the housing having a first end portion and a second end portion;
the first end portion of the housing defining an input configured to receive the heated smoke or vapor, wherein the input opens into the at least one chamber in the housing;
a heat transfer material located in the at least one chamber in the housing and configured to cool the heated smoke or vapor as it passes through the at least one chamber in the housing;
the second end portion of the housing defining an output configured to release the cooled smoke or vapor for being inhaled by a subject; and
a sensor configured to measure at least one of a duration of time that a Peltier device was energized, or temperature, purity, $CO_2$ levels, contamination level, flow, volume, or change in pressure of the cooled smoke or vapor, wherein the sensor is between the heat transfer material and the output.

* * * * *